United States Patent
Ganschow

(10) Patent No.: US 8,318,052 B2
(45) Date of Patent: Nov. 27, 2012

(54) DIKETOPYRROLOPYRROLE COCRYSTALS WITH HIGH TRANSPARENCY

(75) Inventor: Matthias Ganschow, Wiesbaden (DE)

(73) Assignee: Clariant Finance (BVI) Limited, Tortola (VG)

( * ) Notice: Subject to any disclaimer, the term of this patent is extended or adjusted under 35 U.S.C. 154(b) by 142 days.

(21) Appl. No.: 12/526,922

(22) PCT Filed: Jan. 17, 2008

(86) PCT No.: PCT/EP2008/000306
§ 371 (c)(1),
(2), (4) Date: Aug. 12, 2009

(87) PCT Pub. No.: WO2008/101570
PCT Pub. Date: Aug. 28, 2008

(65) Prior Publication Data
US 2010/0119966 A1 May 13, 2010

(30) Foreign Application Priority Data
Feb. 19, 2007 (DE) .......................... 10 2007 008 140

(51) Int. Cl.
*F21V 9/00* (2006.01)
*G02B 5/02* (2006.01)
*G02C 7/10* (2006.01)
*G02F 1/361* (2006.01)
*G03B 11/00* (2006.01)
*C08K 5/00* (2006.01)
*C09D 11/00* (2006.01)
*C07D 243/08* (2006.01)
*G03G 9/00* (2006.01)

(52) U.S. Cl. .................... 252/582; 106/31.6; 106/31.65; 106/31.78; 106/494; 106/498; 252/586; 430/108.21; 524/92; 548/453

(58) Field of Classification Search ................ 252/586, 252/582; 106/31.6, 31.72, 498, 31.65, 494, 106/31.78; 430/108.21; 548/453; 524/92, 524/597, 720
See application file for complete search history.

(56) References Cited

U.S. PATENT DOCUMENTS

| 4,579,949 A * | 4/1986 | Rochat et al. ................. 546/167 |
| 4,720,305 A * | 1/1988 | Iqbal et al. ..................... 106/494 |
| 5,354,869 A * | 10/1994 | Langhals et al. .............. 548/453 |
| 5,476,949 A * | 12/1995 | Wallquist et al. ............. 548/453 |
| 5,869,625 A * | 2/1999 | Jaffe et al. .......................... 8/639 |
| 6,469,147 B2 | 10/2002 | Nickel et al. |
| 6,517,630 B1 * | 2/2003 | Grandidier et al. ........... 106/498 |
| 7,135,266 B2 | 11/2006 | Baur et al. |
| 7,347,894 B2 * | 3/2008 | Yanagimoto et al. ......... 106/496 |
| 2001/0029294 A1 | 10/2001 | Nickel et al. |
| 2003/0083410 A1 | 5/2003 | Baur et al. |
| 2006/0185558 A1 * | 8/2006 | Saikatsu et al. ............... 106/493 |
| 2010/0119966 A1 * | 5/2010 | Ganschow ............... 430/108.21 |
| 2010/0213421 A1 | 8/2010 | Ganschow et al. |
| 2010/0219384 A1 * | 9/2010 | Reipen et al. ................. 252/582 |

FOREIGN PATENT DOCUMENTS

| CH | EP0794235 A1 * | 2/1997 |
| EP | 0094911 | 11/1983 |
| EP | 0181290 | 5/1985 |
| EP | 0640603 | 3/1995 |
| EP | 0962499 | 12/1999 |
| EP | 1257602 | 11/2002 |
| WO | WO02/085987 A1 * | 10/2002 |

OTHER PUBLICATIONS

PCT International Search Report for PCT/EP 2008/000306 mailed Jun. 5, 2008.
English Translation of the PCT Written Opinion of the International Searching Authority for PCT/EP 2008/000306, mailed Sep. 17, 2009.

* cited by examiner

*Primary Examiner* — Ling Choi
(74) *Attorney, Agent, or Firm* — Anthony A. Bisulca

(57) ABSTRACT

The present invention relates to a pigment composition composed of compounds of the formula (I), (II) and (III) with a novel crystal modification, to their preparation and to the use of this novel product as a pigment. For many applications of organic pigments, for example the coloring of metallic lacquers or the use thereof in color filters, a very high transparency is required. To produce color filters, for example, particularly fine pigments are used, in order to substantially rule out the particle scattering which leads to a lowering of the contrast ratio. The commercially available products, however, do not always meet all requirements of the art. More particularly, there was a need for improvement with regard to the transparency and the associated fineness of the pigment crystals, and also the color purity (chroma).

8 Claims, No Drawings

DIKETOPYRROLOPYRROLE COCRYSTALS WITH HIGH TRANSPARENCY

The present invention relates to a pigment composition comprising compounds of formula (I), (II) and (III) having a novel crystal form, to its preparation and to the use of this novel product as a pigment.

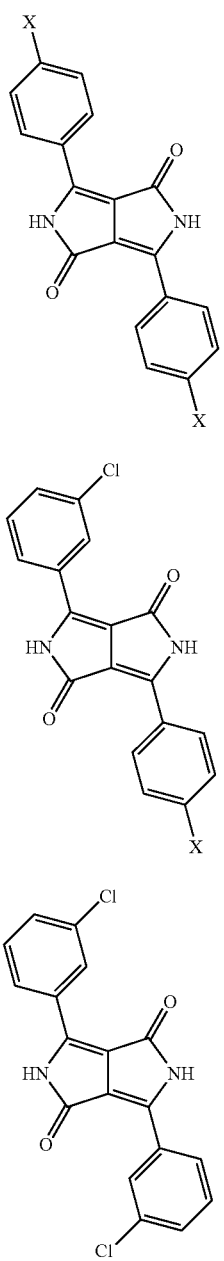

There are many uses where organic pigments are required to have a very high transparency, as in the coloration of metallic coatings or the use in color filters for example. Color filters, for example, are manufactured using particularly finely divided pigments in order that particle scattering, which leads to a reduction in contrast ratio, may be substantially foreclosed.

Commercially available products do not always meet all technical requirements. More particularly, there is a need for improvement with regard to transparency and the associated fine state of subdivision of the pigment crystals, and also chroma.

EP-A-0 094 911 discloses pigment compositions of diketopyrrolopyrroles (DPPs) obtainable by mixed synthesis from two different nitriles A and B and succinic diesters wherein 1 mol of succinic diester is reacted with 1 mol each of two different nitriles. Example 34 describes the reaction of 1 mol of succinic ester with 1 mol of 3-chlorobenzonitrile and 1 mol of 4-chlorobenzonitrile.

EP-A-0 181 290 discloses pigment compositions of diketopyrrolopyrroles (DPPs) obtainable by mixed synthesis from two different nitriles A and B and succinic diesters wherein the molar fractions of the nitriles disclosed in the examples range from 88 to 99.9 mol % of A:12 to 0.1 mol % of B. Mixed syntheses proceeding from 3- and 4-chlorobenzonitriles are not specifically described.

EP-A-0 962499 (Example 42) discloses a pigment composition obtained by mixed synthesis from 50 mol % of 3-chlorobenzonitrile and 50 mol % of 4-chlorobenzo-nitrile with succinic diesters in the presence of a crystal growth inhibitor.

WO 2002/085 987 (Example 1e) discloses a pigment composition obtained by mixed synthesis from 70 mol % of 3-chlorobenzonitrile and 30 mol % of 4-chloro-benzonitrile and acid precipitation of the pigment alkali salt.

It is an object of the present invention to provide a diketopyrrolopyrrole pigment composition of orange to red color that has high transparency and a fine state of subdivision on the part of the pigment crystals as well as high cleanness of hue and brilliance.

We have found that this object is achieved, surprisingly, by a mixed crystal having a certain mixing ratio of bis(4-X-phenyl)diketopyrrolopyrrole (I), (3-chlorophenyl)-(4-X-phenyl)diketopyrrolopyrrole (II) and bis(3-chlorophenyl)diketopyrrolopyrrole (III), and also its process of preparation.

The present invention accordingly provides a mixed crystal comprising compounds of formula (I), (II) and (III),

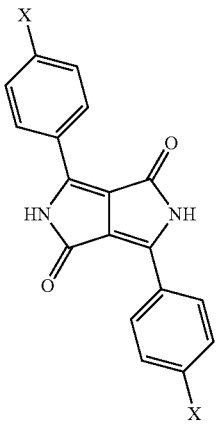

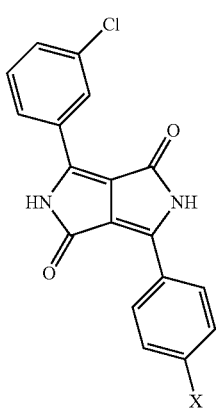

(II)

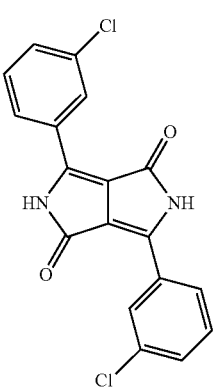

(III)

obtainable by reacting a succinic diester with a mixture comprising 97 to 80 mol % of 3-chlorobenzonitrile and 3 to 20 mol % of 4-X-benzonitrile, where X=chlorine, methyl or nitrile, the molar fractions of said 3-chloro- and 4-X-benzonitriles summing to 100 mol %. Preferably, X is chlorine.

Preference is given to mixed crystals obtainable by reacting a succinic diester with a mixture comprising 95 to 83 mol % of 3-chlorobenzonitrile and 5 to 17 mol % of 4-X-benzonitrile, the molar fractions of said 3-chloro- and 4-X-benzonitriles summing to 100 mol %.

It was found that, surprisingly, the mixed crystals of the present invention have a previously unknown, novel mixed crystal form.

As used herein, the term "mixed crystal" is to be understood as including the meaning of "solid solution". The properties of mixed crystals differ not only from the properties of the individual components but also from the properties of the physical mixtures of the individual components. More particularly, the x-ray powder diagrams of mixed crystals differ from those of the corresponding physical mixtures and from the sum total of the powder diagrams of the individual compounds.

The novel mixed crystal form is notable for an x-ray diffraction diagram which differs from the previously known forms obtained from mixed syntheses from 3- and 4-X-benzonitriles, specifically by a characteristic line at 18.5 (Cu—$K_\alpha$ radiation, 2 theta values in degrees, measuring accuracy +/−0.2°.

The crystal form of the present invention is characterized by the following x-ray powder diagram (Cu—$K_\alpha$ radiation, 2 theta values in degrees, measuring accuracy +/−0.2°, intensities: vs=very strong, s=strong, m=medium, w=weak, all other lines very weak):

| 2 theta: | relative intensity: |
|---|---|
| 5.8 | s |
| 13.2 | s |
| 14.9 | w |
| 16.3 | w |
| 18.5 | m |
| 20.9 | w |
| 24.1 | m |
| 25.7 | s |
| 27.4 | s |
| 29.7 | m |

The mixed crystals of the present invention are obtainable in a fine state of subdivision that corresponds to a BET surface area of 90 to 150 $m^2/g$, preferably 92 to 130 $m^2/g$.

The present invention also provides a process for preparing the mixed crystals of the present invention by reacting a succinic diester with 3-chlorobenzonitrile and 4-X-benzonitrile in the abovementioned proportions in an organic solvent in the presence of a strong base and at elevated temperature to form a pigment alkali salt, subsequent hydrolysis of the pigment alkali salt in water and/or alcohol and optionally subsequent solvent finish.

The overall concentration of nitriles in the organic solvent is advantageously 0.5 to 5 mol/l.

The molar ratio of strong base to succinic diester is advantageously 0.1 to 10 mol of base per 1 mol of succinic diesters.

The reaction temperature for forming the pigment alkali salt is advantageously 60 to 140° C., preferably 80 to 120° C.

The succinic diesters to be used can be dialkyl, diaryl or monoalkyl monoaryl esters, and the dialkyl and diaryl succinate esters may also be asymmetrical. Preference is given to symmetrical succinic diesters, in particular symmetrical dialkyl succinate esters. Aryl in a diaryl succinate or monoaryl monoalkyl succinate, is in particular phenyl which is unsubstituted or substituted by 1, 2 or 3 substituents selected from the group consisting of halogen, such as chlorine, $C_1$-$C_6$-alkyl, such as methyl, ethyl, isopropyl, tert-butyl or tert-amyl, and $C_1$-$C_6$-alkoxy, such as methoxy or ethoxy. Aryl is preferably unsubstituted phenyl. Alkyl in a dialkyl succinate or monoalkyl monoaryl succinate can be unbranched, branched or cyclic, preferably branched, and preferably contain 1 to 18, in particular 1 to 12, especially 1 to 8 and more preferably 1 to 5 carbon atoms. Alkyl is preferably secondary or tertiary alkyl, for example isopropyl, sec-butyl, tert-butyl, tert-amyl, cyclohexyl, heptyl, 2,2-dimethylhexyl, octyl, decyl, dodecyl, tetradecyl or octadecyl.

Examples of succinic diesters are dimethyl succinate, diethyl succinate, dipropyl succinate, dibutyl succinate, dipentyl succinate, dihexyl succinate, diheptyl succinate, dioctyl succinate, diisopropyl succinate, di-sec-butyl succinate, di-tert-butyl succinate, di-tert-amyl succinate, di-[1,1-dimethylbutyl] succinate, di-[1,1,3,3-tetramethylbutyl] succinate, di-[1,1-dimethylpentyl] succinate, di-[1-methyl-1-ethylbutyl] succinate, di-[1,1-diethylpropyl] succinate, diphenyl succinate, di-[4-methylphenyl] succinate, di-[2-methylphenyl] succinate, di-[4-chlorophenyl] succinate, di-[2,4-dichlorophenyl] succinate, monoethyl monophenyl succinate, dicyclohexyl succinate.

Symmetrical dialkyl succinates wherein alkyl is branched and contains 3 to 5 carbon atoms are used in particular.

The reaction of the succinic diester with the nitrile is carried out in an organic solvent. Examples of suitable solvents are primary, secondary or tertiary alcohols having 1 to 10 carbon atoms, such as methanol, ethanol, n-propanol, isopropanol, n-butanol, sec-butanol, tert-butanol, pentanols, such as n-pentanol or 2-methyl-2-butanol, hexanols, such as 2-methyl-2-pentanol or 3-methyl-3-pentanol, 2-methyl-2-hexanol, 3-ethyl-3-pentanol, octanols, such as 2,4,4-trimethyl-2-pentanol, cyclohexanol, or glycols, such as ethylene glycol, diethylene glycol, propylene glycol, dipropylene glycol or glycerol, or polyglycols, such as polyethylene glycols or polypropylene glycols, ethers, such as methyl isobutyl ether, tetrahydrofuran, dimethoxyethane or dioxane, glycol ethers, such as monomethyl or monoethyl ethers of ethylene glycol or of propylene glycol, diethylene glycol monomethyl ether or diethylene glycol monoethyl ether, butyl glycols or methoxybutanol, dipolar aprotic solvents, for example acid amides such as dimethylformamide, N,N-dimethylacetamide or N-methylpyrrolidone, urea derivatives such as tetramethylurea, aliphatic or aromatic hydrocarbons, such as cyclohexane or benzene or alkyl-, alkoxy-, nitro- or halogen-substituted benzene, such as toluene, xylenes, ethylbenzene, anisole, nitrobenzene, chlorobenzene, o-dichlorobenzene or 1,2,4-trichlorobenzene, aromatic N-heterocycles, such as pyridine, picoline or quinoline, and also hexamethylphosphoramide, 1,3-dimethyl-2-imidazolidinone, dimethyl sulfoxide or sulfolane.

The pigment alkali metal salt is prepared in the presence of a strong base. Suitable strong bases are in particular the alkali metal salts themselves, such as lithium, sodium or potassium, or alkali metal amides, such as lithium-, sodium- or potassium amide, or alkali metal hydrides, such as lithium, sodium or potassium hydride, or alkaline earth metal or alkali metal alkoxides derived in particular from primary, secondary or tertiary aliphatic alcohols having 1 to 10 carbon atoms, such as for example lithium methoxide, sodium methoxide, potassium methoxide, lithium ethoxide, sodium ethoxide, potassium ethoxide, lithium n-propoxide, sodium n-propoxide, potassium n-propoxide, lithium isopropoxide, sodium isopropoxide, potassium isopropoxide, lithium n-butoxide, sodium n-butoxide, potassium n-butoxide, lithium sec-butoxide, sodium sec-butoxide, potassium sec-butoxide, lithium tert-butoxide, sodium tert-butoxide, potassium tert-butoxide, lithium 2-methyl-2-butoxide, sodium 2-methyl-2-butoxide, potassium 2-methyl-2-butoxide, lithium 2-methyl-2-pentoxide, sodium 2-methyl-2-pentoxide, potassium 2-methyl-2-pentoxide, lithium 3-methyl-3-pentoxide, sodium 3-methyl-3-pentoxide, potassium 3-methyl-3-pentoxide, lithium 3-ethyl-3-pentoxide, sodium 3-ethyl-3-pentoxide or potassium 3-ethyl-3-pentoxide. Mixtures of the bases mentioned can also be used.

Preference is given to alkali metal alkoxides where alkali metal is in particular sodium or potassium and the alkoxide preferably derives from a secondary or tertiary alcohol. Particularly preferred strong bases are therefore for example sodium isopropoxide, potassium isopropoxide, sodium sec-butoxide, potassium sec-butoxide, sodium tert-butoxide, potassium tert-butoxide, sodium tert-amoxide and potassium tert-amoxide. The alkali metal alkoxides can also be prepared in situ by reacting the appropriate alcohol with the alkali metal, alkali metal hydride or alkali metal amide.

To hydrolyze the pigment alkali metal salt, water or one or more organic protic solvents can be used as a hydrolyzing agent. Useful protic solvents include for example alcohols, preferably having 1 to 4 carbon atoms, such as methanol or ethanol. It is also possible to use water and alcohol in any desired combination. The hydrolysis can also be carried out in the presence of organic aprotic solvents. The hydrolysis can be accomplished directly by addition of a hydrolyzing agent to the reaction suspension, or indirectly, by addition of the reaction suspension to the hydrolyzing agent. The hydrolyzing agents water and organic protic solvent can be added and/or initially charged in any desired order and also as mixtures. Concurrent addition of individual components to an initial charge is also possible. It can be of advantage to use a buffer during the hydrolysis, for example a phosphate, acetate, citric acid or triethanolamine buffer.

The temperature at which the hydrolysis is carried out can be in the range from −20° C. to 200° C., preferably in the range from −5 to 180° C. and in particular in the range from 0 to 160° C., if necessary under superatmospheric pressure. The reaction suspension and the hydrolyzing agent can also have different temperatures. For example, the hydrolysis can also be accomplished by means of steam.

The total amount of hydrolyzing agent is advantageously an at least stoichiometric amount based on base. For example, water and/or an organic protic solvent can be used at between 0.5 and 50 parts by weight per 1 part of the pigment formed.

The mixed crystals of the present invention can subsequently also be finished without the crystal form changing. Depending on the conditions of the finish operation, the finely divided particles can grow again, so that the conditions of the finish operation have to be appropriately adjusted to the desired field of use. Finish conditions which lead to more opaque particles are known to one skilled in the art and are described in WO 02/085 987 for example.

Finish conditions which substantially preserve the fine state of subdivision achieved according to the present invention are described in EP-A-0 640 603 for example.

In a preferable procedure, the pigment suspension obtained in the hydrolysis of the pigment alkali metal salt is heated to a temperature of 50 to 150° C., in particular 80 to 130° C., if appropriate under superatmospheric pressure, for 0.1 to 8 hours, in particular 0.5 to 6 hours. The presence of surface-active agents which inhibit crystal growth can be advantageous.

Pigment dispersants, surface-active agents, defoamers, extenders or other admixtures can be added at any stage of the process to facilitate formation of mixed crystals, to stabilize the mixed crystals, to inhibit crystal growth, to improve the coloristic properties and to achieve defined coloristic effects, provided these added materials do not impair the advantages associated with the present invention. Mixtures of these added materials can also be used. The materials which are added can be added in one or more portions. The materials which are added can be added at every stage of the synthesis or the various aftertreatments, or after the aftertreatments. The most suitable point in time has to be determined beforehand by means of range-finding tests.

It is also possible for one or more of the recited operations for preparing the pigment compositions of the present invention to be carried out in a microreactor, for example as described in EP-A-1 257 602.

The mixed crystals of the present invention can in principle be used for pigmentation of all macromolecular organic materials of natural or synthetic origin, for example plastics, resins, coatings, in particular metallic coatings, paints, printing inks, electrophotographic toners and developers, electret materials, color filters and also liquid inks, in particular inkjet inks.

Macromolecular organic materials which can be pigmented with the mixed crystals of the present invention are for example cellulose compounds, such as for example cellulose ethers and esters, such as ethylcellulose, nitrocellulose, cellulose acetates or cellulose butyrates, natural binders, such as for example fatty acids, fatty oils, resins and transformation products thereof, or synthetic resins, such as polycondensates, polyadducts, addition polymers and addition copolymers, such as for example aminoplasts, in particular urea- and melamine-formaldehyde resins, alkyd resins, acrylic resins, phenoplasts and phenolic resins, such as novolaks or resols, urea resins, polyvinyls, such as polyvinyl alcohols, polyvinyl acetals, polyvinyl acetates or polyvinyl ethers, polycarbonates, polyolefins, such as polystyrene, polyvinyl chloride, polyethylene or polypropylene, poly (meth)acrylates and addition copolymers thereof, such as polyacrylic esters or polyacrylonitriles, polyamides, polyesters, polyurethanes, coumarone-indene and hydrocarbon resins, epoxy resins, unsaturated synthetic resins (polyesters, acrylates) having different curing mechanisms, waxes, aldehyde and ketone resins, vulcanized rubber, unvulcanized rubber and its derivatives and latices, casein, silicones and silicone resins; individually or in mixtures.

It is immaterial here whether the macromolecular organic compounds mentioned are present as plastically deformable masses, melts or in the form of spinning solutions, dispersions, coatings, paints or printing inks. Depending on the intended use, it will be found to be advantageous to use the mixed crystals of the present invention as a blend or in the form of preparations or dispersions.

Based on the macromolecular organic material to be pigmented, the mixed crystals of the present invention are usually used in an amount of 0.01% to 30% by weight and preferably 0.1% to 20% by weight.

The mixed crystals of the present invention are also useful as colorants in electrophotographic toners and developers, for example one- or two-component powder toners (also called one- or two-component developers), magnetic toners, liquid toners, addition polymerization toners and also specialty toners. Typical toner binders are addition polymerization, polyaddition and polycondensation resins, such as styrene resins, styrene-acrylate resins, styrene-butadiene resins, acrylate resins, polyester resins, phenol-epoxide resins, polysulfones, polyurethanes, individually or in combination, and also polyethylene and polypropylene, which may each contain still further ingredients, such as charge control agents, waxes or flow assistants, or are subsequently modified with these additions.

The mixed crystals of the present invention are also useful as colorants in inkjet inks having an aqueous or a nonaqueous base and also inkjet inks operating by the hotmelt process.

Inkjet inks contain in general or together 0.5% to 15% by weight and preferably 1.5% to 8% by weight (reckoned dry) of one or more of the mixed crystals of the present invention.

Microemulsion inks are based on organic solvents, water and optionally an additional hydrotropic substance (compatibilizer). Microemulsion inks contain in general 0.5% to 15% by weight and preferably 1.5% to 8% by weight of one or more of the mixed crystals of the present invention, 5% to 99% by weight of water and 0.5% to 94.5% by weight of organic solvent and/or hydrotropic compound.

Solvent based inkjet inks contain preferably 0.5% to 15% by weight of one or more of the mixed crystals of the present invention, 85% to 99.5% by weight of organic solvent and/or hydrotropic compounds.

Hotmelt inks are usually based on waxes, fatty acids, fatty alcohols or sulfonamides which are solid at room temperature and become liquid on heating, the preferred melting range being between about 60° C. and about 140° C. Hotmelt inkjet inks consist essentially for example of 20% to 90% by weight of wax and 1% to 10% by weight of one or more of the mixed crystals of the present invention. They may further contain 0% to 20% by weight of an additional polymer (as "dye dissolver"), 0% to 5% by weight of dispersing auxiliary, 0% to 20% by weight of viscosity modifier, 0% to 20% by weight of plasticizer, 0% to 10% by weight of tackiness additive, 0% to 10% by weight of transparency stabilizer (prevents for example crystallization of waxes) and also 0% to 2% by weight of antioxidant.

More particularly, the mixed crystals of the present invention are useful as colorants for color filters not only for additive color production but also for subtractive color production, as for example in electro-optical systems such as television screens, liquid crystal displays (LCDs), charge coupled devices, plasma displays or electroluminescent displays, which in turn can be active (twisted nematic) or passive (supertwisted nematic) ferroelectric displays or light-emitting diodes, and also as colorants for electronic inks, or e-inks, or electronic paper (e-paper).

To manufacture color filters, whether of the reflecting type or of the transparent type, pigments in the form of a paste or as pigmented photoresists in suitable binders (acrylates, acrylic esters, polyimides, polyvinyl alcohols, epoxys, polyesters, melamines, gelatin, caseins) are applied to the respective LCD components (for example TFT-LCD=Thin Film Transistor Liquid Crystal Displays or for example ((S) TN-LCD=(Super) Twisted Nematic-LCD). As well as high thermal stability, a high pigment purity is also a prerequisite for a stable paste or for a pigmented photoresist.

In addition, the pigmented color filters can also be applied by inkjet printing processes or other suitable printing processes.

The red hues of the mixed crystals of the present invention are very particularly useful for the color filter color set of red-green-blue (RGB). These three colors are present side by side as separate dots of color which, when backlit, produce a full-color picture.

Typical colorants for the red dot are pyrrolopyrrole, quinacridone and azo pigments, for example C.I. Pigment Red 254, C.I. Pigment Red 209, C.I. Pigment Red 175 and C.I. Pigment Orange 38, individually or mixed. The green dot utilizes phthalocyanine colorants, for example C.I. Pigment Green 36 and C.I. Pigment Green 7.

If necessary, the respective color dots will each be admixed with further colors for shading. The red and green dots are preferably admixed with yellow, for example with C.I. Pigment Yellow 138,139,150,151,180 and 213.

It is finally also possible to process the mixed crystal pigment of the present invention by dry mixing with organic or inorganic masses, granules, fibers, powders and other pigments to obtain compositions of matter.

In the examples which follow, percentages and parts are by weight, unless otherwise stated. The x-ray powder diagrams were measured with Cu—$K_\alpha$ radiation, 2 theta values in degrees, measurement accuracy +/−0.2°, and the reported intensities mean: vs=very strong, s=strong, m=medium, w=weak.

COMPARATIVE EXAMPLE 1

50% 3-chlorobenzonitrile, 50% 4-chlorobenzonitrile

A pigment mixture is prepared as described in Example 34 of EP-A-0 094 911 from a mixture of 50 mol % of 3-chlorobenzonitrile and 50 mol % of 4-chlorobenzo-nitrile.

The pigment obtained has a BET surface area of 56 m²/g and the following characteristic lines in the x-ray powder diagram:

| 2 theta: | Relative intensity: |
|---|---|
| 5.8 | s |
| 11.8 | w |
| 13.1 | m |
| 14.4 | s |
| 17.6 | m |
| 20.9 | w |
| 22.1 | w |
| 24.1 | m |
| 24.5 | m |
| 26.9 | s |
| 28.9 | m |

The characteristic novel line of the crystal form of the present invention at 18.5° (+/−0.2) 2 theta is not observed.

COMPARATIVE EXAMPLE 2

70% 3-chlorobenzonitrile, 30% 4-chlorobenzonitrile, acid precipitation

The mixture is prepared as described in Example 1e of WO 02/085987 A1 from a mixture of 70 mol % of 3-chlorobenzonitrile and 30 mol % of 4-chlorobenzonitrile.

The pigment obtained has a BET surface area of 87 m²/g and the following characteristic lines in the x-ray powder diagram:

| 2 theta: | relative intensity: |
|---|---|
| 5.8 | s |
| 13.2 | m |
| 14.3 | m |
| 17.9 | m |
| 22.2 | w |
| 24.1 | m |
| 25.3 | m |
| 26.2 | m |
| 27.2 | s |
| 29.5 | w |

The characteristic novel line of the crystal form of the present invention at 18.5° (+/−0.2) 2 theta is not observed.

COMPARATIVE EXAMPLE 3

70% 3-chlorobenzonitrile, 30% 4-chlorobenzonitrile, precipitation onto water 21.7 parts of 3-chlorobenzonitrile and 9.3 parts of 4-chlorobenzonitrile are introduced into 30% sodium amylate (prepared from 9.3 parts of sodium and 143 parts of amyl alcohol) and heated to 100° C. 30 parts of diisopropyl succinate are added during two hours. After a further four hours at 100° C., the pigment alkali metal salt suspension is cooled down to 80° C. and poured onto hot water at 60° C. The pigment suspension is subsequently conditioned by heating to 95° C. for five hours, filtering off, washing with methanol and water and drying at 75° C. in a drying cabinet to leave a reddish orange pigment.

The pigment obtained has a BET surface area of 73 m²/g and the following characteristic lines in the x-ray powder diagram:

| 2 theta: | relative intensity: |
|---|---|
| 5.9 | s |
| 13.1 | m |
| 14.5 | m |
| 17.9 | m |
| 21.8 | w |
| 24.1 | m |
| 25.9 | s |
| 26.2 | m |
| 27.2 | s |
| 29.7 | w |

The characteristic novel line of the crystal form of the present invention at 18.5° (+/−0.2) 2 theta is not observed.

EXAMPLE 1

Mixed Crystal Formed from 80 mol % of 3-chlorobenzonitrile and 20 mol % of 4-chlorobenzonitrile Comparative Example 3 is repeated except that 24.8 parts of 3-chlorobenzonitrile and 6.2 parts of 4-chlorobenzonitrile are reacted.

The product is isolated and washed with methanol and water to leave a reddish orange pigment.

The pigment obtained has a BET surface area of 103 m²/g and is very much more finely divided than the pigments of Comparative Examples 1 and 3. It has the following characteristic lines in the x-ray powder diagram:

| 2 theta: | relative intensity: |
|---|---|
| 5.7 | s |
| 13.2 | s |
| 14.9 | w |
| 16.3 | w |
| 18.4 | m |
| 20.9 | w |
| 24.2 | m |
| 25.8 | s |
| 27.3 | s |
| 29.8 | m |

The characteristic novel line of the crystal form of the present invention at 18.5° (+/−0.2) 2 theta is observed.

EXAMPLE 2

Mixed Crystal Formed from 83 mol % of 3-chlorobenzonitrile and 17 mol % of 4-chlorobenzonitrile Comparative Example 3 is repeated except that 25.8 parts of 3-chlorobenzonitrile and 5.2 parts of 4-chlorobenzonitrile are reacted. This leaves a reddish orange pigment.

The pigment obtained has a BET surface area of 98 m²/g and is very much more finely divided than the pigments of Comparative Examples 1 and 3. It has the following characteristic lines in the x-ray powder diagram:

| 2 theta: | relative intensity: |
|---|---|
| 5.8 | s |
| 13.2 | s |

-continued

| 2 theta: | relative intensity: |
|---|---|
| 14.9 | w |
| 16.3 | w |
| 18.5 | m |
| 20.9 | w |
| 24.2 | m |
| 25.8 | s |
| 27.3 | s |
| 29.8 | m |

The characteristic novel line of the crystal form of the present invention at 18.5° (+/−0.2) 2 theta is observed.

EXAMPLE 3

Mixed Crystal Formed from 92 mol % of 3-chlorobenzonitrile and 8 mol % of 4-chlorobenzonitrile Comparative Example 3 is repeated except that 28.4 parts of 3-chlorobenzonitrile and 2.6 parts of 4-chlorobenzonitrile are reacted. This leaves a reddish orange pigment.

The pigment obtained has a BET surface area of 99 m²/g and is very much more finely divided than the pigments of Comparative Examples 1 and 3. It has the following characteristic lines in the x-ray powder diagram:

| 2 theta: | relative intensity: |
|---|---|
| 5.9 | s |
| 13.2 | s |
| 14.9 | w |
| 16.3 | w |
| 18.6 | m |
| 20.9 | w |
| 24.1 | m |
| 25.7 | s |
| 27.4 | s |
| 29.8 | m |

The characteristic novel line of the crystal form of the present invention at 18.5° (+/−0.2) 2 theta is observed.

EXAMPLE 4

Mixed Crystal Formed from 83 mol % of 3-chlorobenzonitrile and 17 mol % of 4-methylbenzonitrile Comparative Example 3 is repeated except that 25.8 parts of 3-chlorobenzonitrile and 5.2 parts of 4-methylbenzonitrile are reacted. This leaves a reddish orange pigment.

The pigment obtained has a BET surface area of 102 m²/g and is very much more finely divided than the pigments of Comparative Examples 1 and 3.

The characteristic novel line of the crystal form of the present invention at 18.5° (+/−0.2) 2 theta is observed.

EXAMPLE 5

Mixed Crystal Formed from 83 mol % of 3-chlorobenzonitrile and 17 mol % of terephthalonitrile Comparative Example 3 is repeated except that 25.8 parts of 3-chlorobenzonitrile and 5.2 parts of 4-terephthalonitrile are reacted. This leaves a reddish orange pigment.

The pigment obtained has a BET surface area of 109 m²/g and is very much more finely divided than the pigments of Comparative Examples 1 and 3. The characteristic novel line of the crystal form of the present invention at 18.5° (+/−0.2) 2 theta is observed.

The BET surface areas of the pigments prepared in the preceding examples are reported in the table which follows:

| Sample | BET surface area |
|---|---|
| Comparative Example 1 | 56 m²/g |
| Comparative Example 2 | 87 m²/g |
| Comparative Example 3 | 73 m²/g |
| Inventive Example 1 | 103 m²/g |
| Inventive Example 2 | 98 m²/g |
| Inventive Example 3 | 99 m²/g |
| Inventive Example 4 | 102 m²/g |
| Inventive Example 5 | 109 m²/g |

Inventive Examples 1 to 5 are very much more finely crystalline than Comparative Examples 1 to 3.

Illustrative uses:

To determine the color strength and transparency of the pigment mixtures, the pigments obtained were fully dispersed in a transparent alkyd-melamine baking finish system.

To determine transparency, a pigmented alkyd-melamine baking finish was applied as a masstone coating to a white piece of cardboard showing a black bar side by side together with the sample to be compared, air dried for 30 min and then baked at 140° C. for 30 min. Transparency was evaluated by comparing the hiding power of the two applied pigments on top of a black background.

To determine color strength, a reduction coating was prepared by mixing 6.0 g of the alkyd-melamine masstone coating with 20.0 g of a 30% white varnish. The reduction coating obtained was applied to a white piece of cardboard together with and next to the sample to be compared, air dried for 30 min and then baked at 140° C. for 30 min. Color strength and its measurement is defined in DIN EN ISO 787-26.

The color strengths, chroma (color cleanness) and transparency of the pigments prepared in the above examples are reported in the table below. The pigment of Example 1 was used as standard for the color strength (100%), the chroma AC (cleanness) (ΔC=0) and the transparency.

Transparency was assessed as follows:
+VI significantly more hiding
+V substantially more hiding
+IV distinctly more hiding
+III markedly more hiding
+II somewhat more hiding
+I a trace more hiding
I=I approximately equal to
−I a trace more transparent
−II somewhat more transparent
−III markedly more transparent
−IV distinctly more transparent
−V substantially more transparent
−VI significantly more transparent

| Sample | Color strength | ΔC | Transparency |
|---|---|---|---|
| Comparative Example 1 | 80% | −3.4 | +V/substantially more hiding |
| Comparative Example 2 | 104% | −4.15 | −II/somewhat more transparent |

-continued

| Sample | Color strength | ΔC | Transparency |
|---|---|---|---|
| Comparative Example 3 | 82% | −1.2 | +V/substantially more hiding |
| Inventive Example 1 | 100% | +/−0 | Reference |
| Inventive Example 2 | 100% | −0.2 | −II/somewhat more transparent |
| Inventive Example 3 | 102% | −0.4 | −II/somewhat more transparent |

Comparative Examples 1, 2 and 3 are very much duller (ΔC<<−1.0) than Inventive Examples 1 to 3. Comparative Examples 1 and 3 are also much more hiding than Inventive Examples 1 to 3.

What is claimed is:

1. A mixed crystal comprising compounds of formula (I), (II), (III),

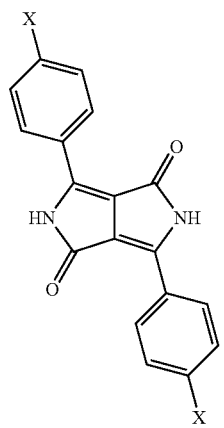
(I)

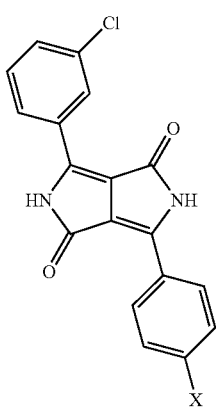
(II)

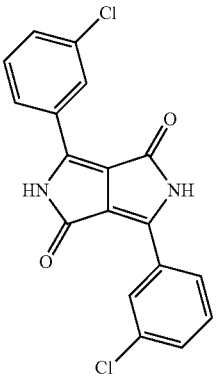
(III)

obtained by reacting a succinic diester with a nitrile mixture comprising 95 to 83 mol % of 3-chlorobenzonitrile and 5 to 17 mol % of 4-X-benzonitrile, wherein X=chlorine, methyl or nitrile and the molar fractions of said 3-chloro- and 4-X-benzonitriles summing to 100 mol %, and wherein the mixed crystal has a BET surface area of 90 to 150 $m^2/g$.

2. The mixed crystal as claimed in claim 1, wherein X is chlorine.

3. The mixed crystal as claimed in claim 1, wherein the mixed crystal has a characteristic line in a x-ray diffraction diagram at 2 theta 18.5°+/−0.2, measured with Cu—$K_\alpha$ radiation.

4. The mixed crystal as claimed in claim 1, wherein the main signals in a x-ray powder diagram:

| 2 theta: | relative intensity: |
|---|---|
| 5.8 | s |
| 13.2 | s |
| 14.9 | w |
| 16.3 | w |
| 18.5 | m |
| 20.9 | w |
| 24.1 | m |
| 25.7 | s |
| 27.4 | s |
| 29.7 | m | wherein the x-ray powder diagram is Cu—$K_\alpha$ radiation, 2 theta values in degrees, measuring accuracy +/−0.2°, intensities: s=strong, m=medium, w=weak).

5. A process for preparing a mixed crystal as claimed in claim 1, comprising the steps of reacting a succinic diester with 95 to 83 mol % of 3-chlorobenzonitrile and 5 to 17 mol % of 4-X-benzonitrile in an organic solvent in the presence of a strong base and at elevated temperature to form a pigment alkali salt, hydrolyzing the pigment alkali salt in water, alcohol or both to obtain the mixed crystal and optionally solvent finishing the hydrolyzed pigment alkali salt, wherein X=chlorine, methyl or nitrile.

6. A macromolecular organic material of natural or synthetic origin pigmented by a mixed crystal as claimed in claim 1.

7. A composition pigmented by a mixed crystal as claimed in claim 1, wherein the composition is in a form selected from the group consisting of plastics, resins, coatings, paints, printing inks, electrophotographic toners, electrophotographic developers, color filters and liquid inks.

8. A color filter, metallic coating or inkjet ink pigmented by the mixed crystal as claimed in claim 1.

* * * * *